Figure 1:
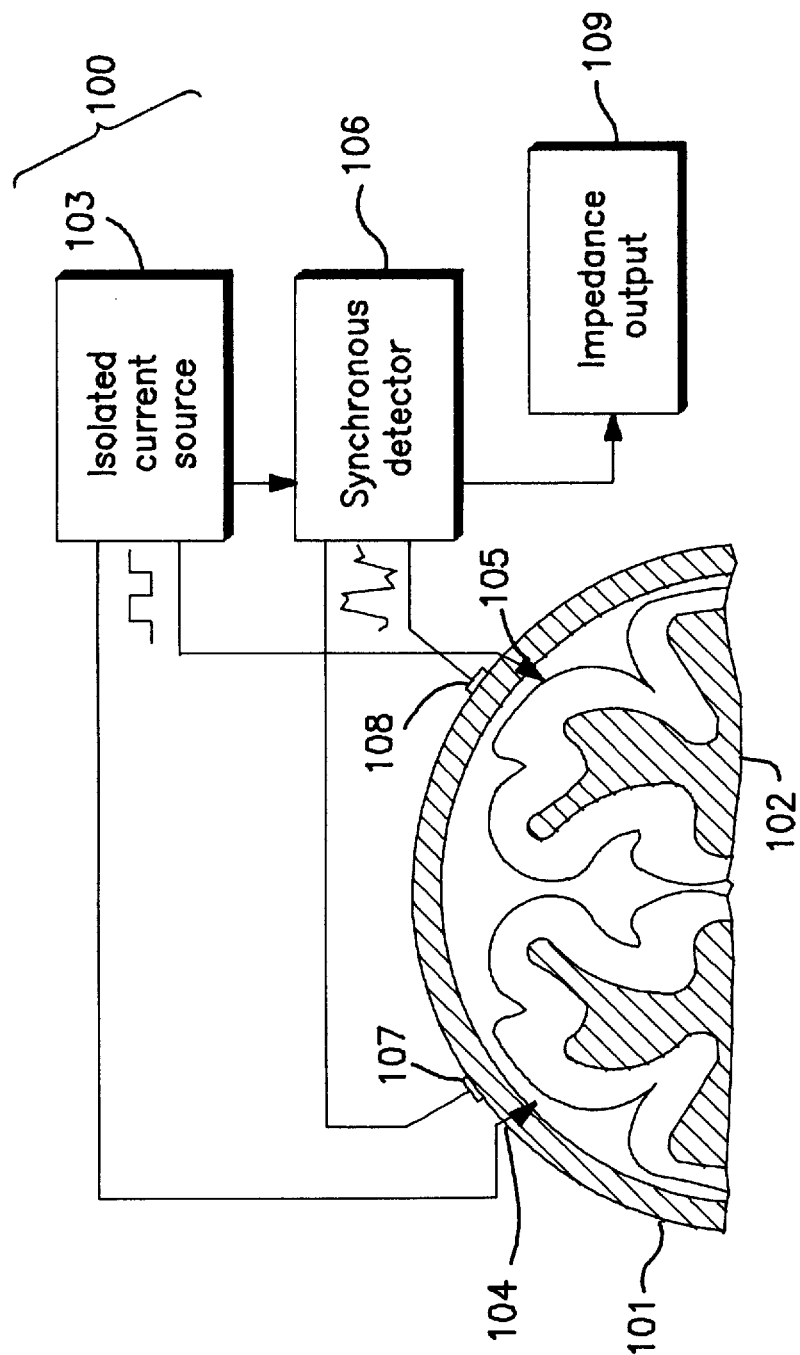

United States Patent [19]
Williams

[11] Patent Number: 5,807,270
[45] Date of Patent: Sep. 15, 1998

[54] BRAIN DAMAGE MONITOR

[76] Inventor: Christopher Edward Williams, C/- Auckland UniServices Ltd, UniServices House, 58 Symonds St., Auckland, New Zealand

[21] Appl. No.: 750,794
[22] PCT Filed: Dec. 20, 1994
[86] PCT No.: PCT/NZ94/00147
  § 371 Date: Dec. 18, 1996
  § 102(e) Date: Dec. 18, 1996
[87] PCT Pub. No.: WO95/35060
  PCT Pub. Date: Dec. 28, 1995

[30]     Foreign Application Priority Data

Jun. 20, 1994 [NZ]  New Zealand ............................ 260798

[51] Int. Cl.⁶ ...................................................... A61B 5/05
[52] U.S. Cl. ............................................................ 600/547
[58] Field of Search .................................... 600/544, 547

[56]                References Cited

U.S. PATENT DOCUMENTS 3,566,233  2/1971  Kahn et al. ................................ 73/190
4,424,816  1/1984  Callahan et al. ........................ 128/731
4,690,149  9/1987  Ko ............................................ 128/653
5,224,490  7/1993  Allen et al. .............................. 128/775

*Primary Examiner*—Max Hindenburg
*Assistant Examiner*—Pamela A. Wingood
*Attorney, Agent, or Firm*—Young & Thompson

[57]                ABSTRACT

An impedance monitor (100) is adapted for use in long-term monitoring of intracellular (neuronal) swelling in the brains (102) of mammals over periods of hours or days. The monitor has an electrically isolated current source (103), supplying a one microampere AC square waveform at 200 Hz. This current is passed through an outer pair of electrodes (104, 105) of a four-electrode arrangement having skin electrodes, extradural electrodes, or in some cases surface electrodes embedded in surgical retractors. Sensing electrode pairs (107, 108) may also detect EEG activity. Impedance changes are displayed graphically (109). Multiple electrode arrays may be used for localization of affected portions of the brain. Even trans-cranially measured impedances reflect intracellular oedema and are clinically useful indicators of treatment efficacy and outcome in cases of ischaemia, asphyxia, trauma, and the like.

10 Claims, 11 Drawing Sheets

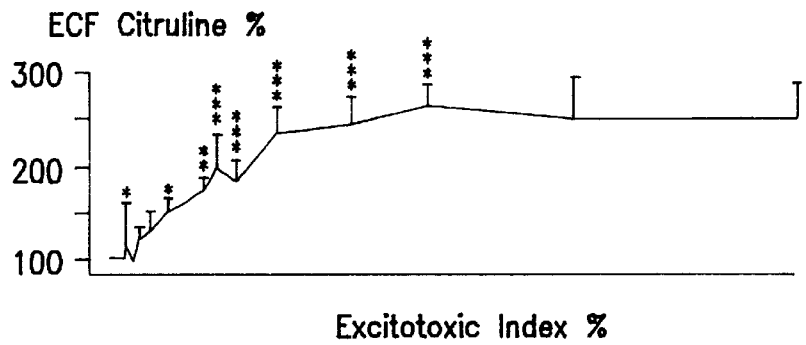
FIG. 10A
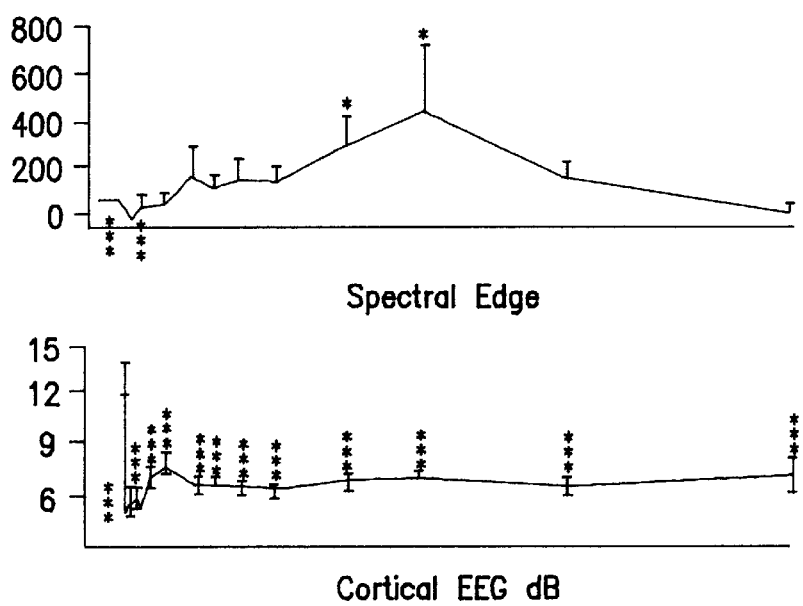
FIG. 10B
FIG. 10C
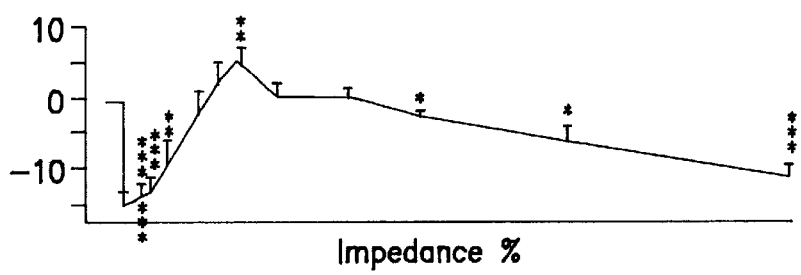
FIG. 10D
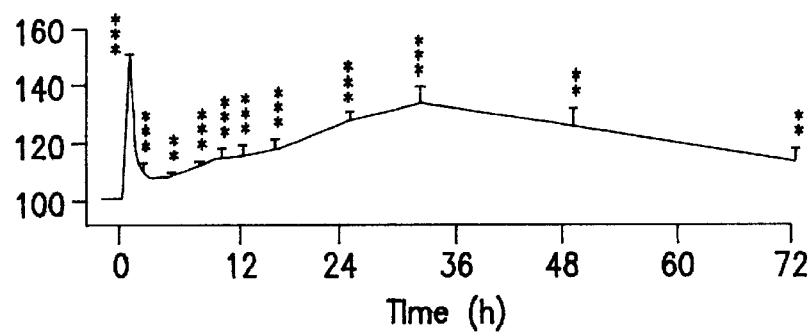
FIG. 10E

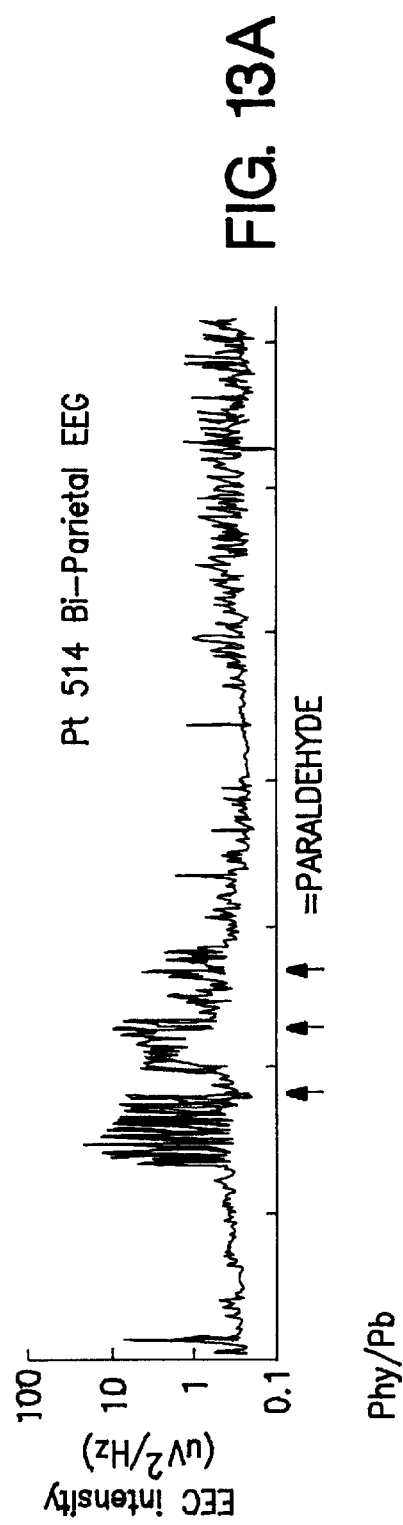
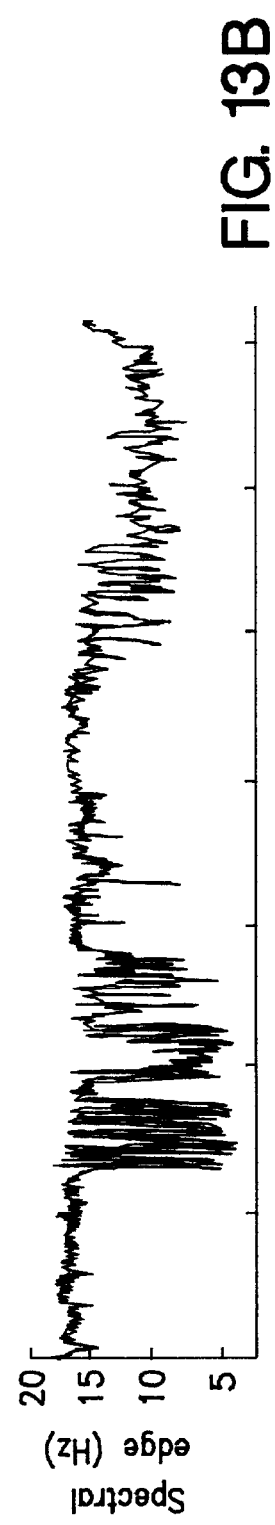
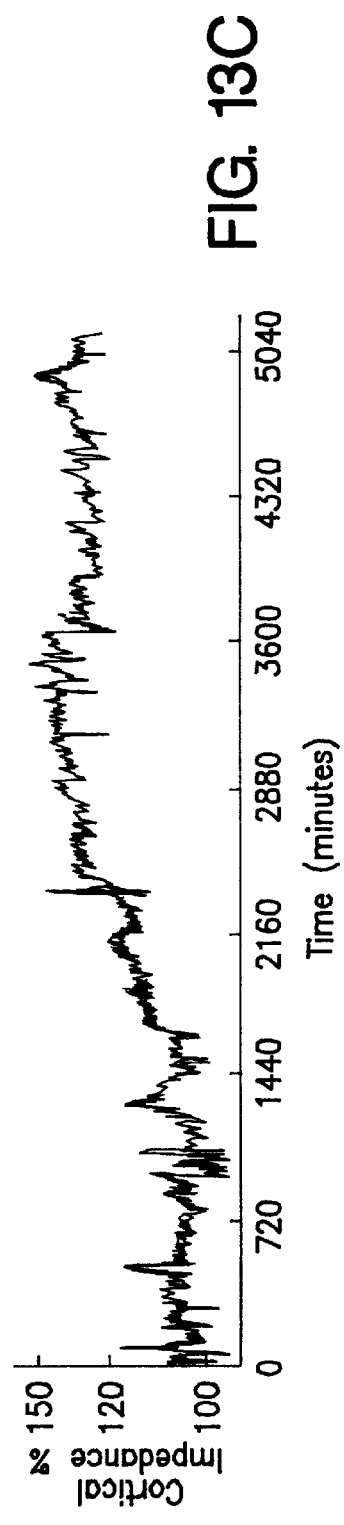
FIG. 13A
FIG. 13B
FIG. 13C

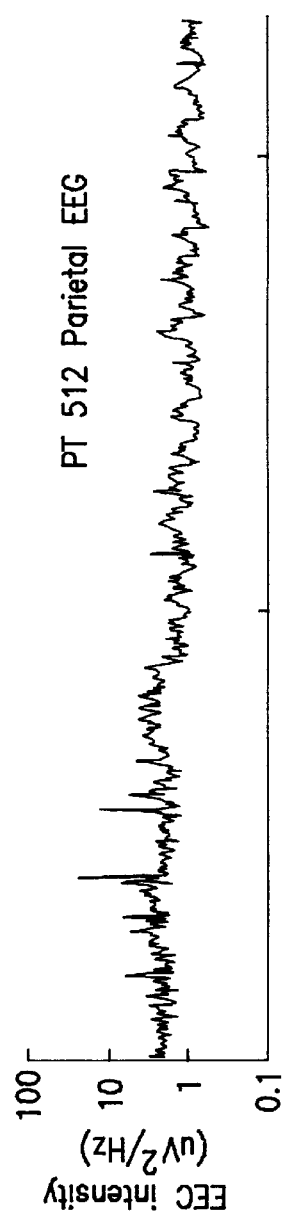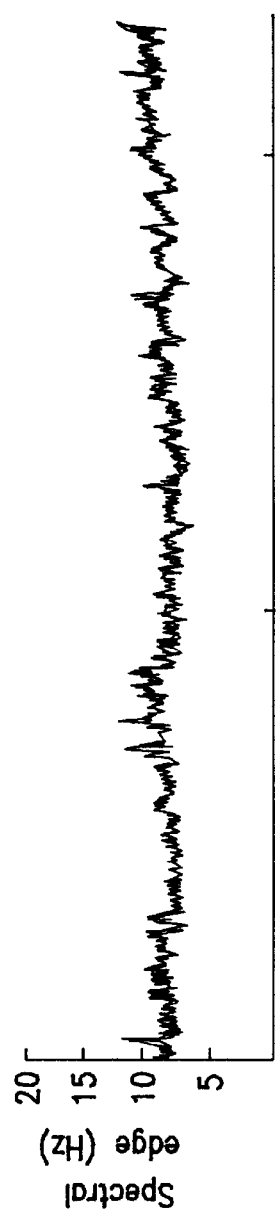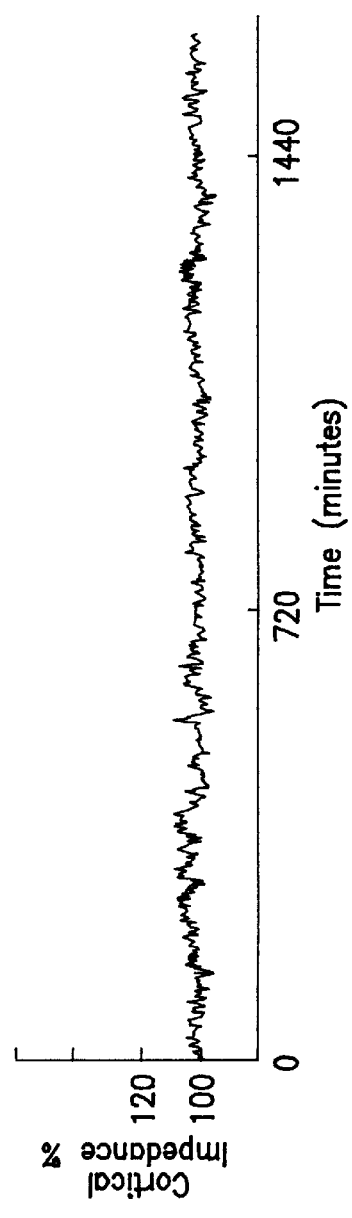

BRAIN DAMAGE MONITOR

FIELD OF THE INVENTION

This invention relates to the monitoring and management of oedema in certain tissues, in particular intracellular oedema within the brains of mammals, and the assessment of swelling following injury by me of electrical impedance measurements. It is adapted for long-term monitoring using suitable externally applied electrodes and also short-term monitoring of tissue trauma during surgery where surgical tools having embedded electrodes are used. The invention discloses mpedance monitoring equipment, and a method for use of the equipment.

BACKGROUND

The monitoring of patients with acute head injuries, whether caused by externally induced trauma such as birth or accident, or by circulatory problems, has hitherto relied upon clinical signs but these may not appear until a time at which the damage may have become at least partially irreversible.

Electroencephalography (EEG) tests preferably also including a frequency analysis device to reduce the data and indicate electrical activity is more suitable, though impractical outside a controlled environment. (Reliable EEG measurements require electrical screening from outside interference, a motionless subject, and relatively complex equipment).

Cerebral oedema is a particular problem during brain surgery, where manipulation, such as retraction of parts of the brain almost inevitably involves some alteration to the circulation of blood and extracellular fluids. At present the practice is to release retractors from time to time on an empirical basis, not knowing whether the chosen time is needlessly early or too late.

It appears that cerebral oedema is particularly significant when it occurs intracellularly, within neurones. It appears that there is a kind of "self-destruct" process affecting neurones, occurring over a period after some types of CNS injury, the effects of which can be ameliorated by clinical management.

There is a clear need for a better detection procedure for the onset of cerebral oedema, so that steps to alleviate it may be taken as soon as possible and even before the appearance of clinical signs, thereby providing for increased survival and better long-term prospects of patients.

OBJECT

It is an object of the present invention to provide an improved system for the measurement of oedema of the central nervous system, or one which will at least provide the public with a useful choice.

STATEMENT OF THE INVENTION

In one broad aspect the invention provides means capable of repeatedly measuring the impedance of the whole brain or parts thereof of living mammals, thereby indicating the state of normality of the tissues under test More particularly the test indicates the amount of extracellular fluid present.

Preferably the measurement procedure is non-invasive and does not interfere with brain function.

In a related aspect the invention provides impedance measuring equipment suitable for use in cranial or intracranial impedance measurements of nervous tissue.

Preferably a four-electrode test arrangement is used.

Preferably a synchronous detector is used to detect an AC voltage developed as a result of an alternating current applied to the tissue under test.

Preferably the frequency used is a frequency between 3 Hz and 3 KHz.

More preferably the frequency used is between 30 Hz and 150 Hz.

Preferably the current is between ten microamperes and 0.1 microamperes.

More preferably the current is of the order of one microampere.

Preferably the current used is physiologically acceptable and is substantially below potentially harmful limits, even if used continuously over a period.

Preferably the impedance measurement is averaged over time so that artefacts resulting from effects such as pulsatile blood flow or inadvertent muscle movements are substantially not apparent.

Preferably the equipment is portable and preferably it is electrically isolated, Optionally it may simply indicate the absence or presence of a state of oedema, though preferably an analogue indication is provided, More preferably a graphical indication showing the time course of the measured impedance is provided so that the time course or evolution of a possible state of oedema is made apparent.

In another broad aspect the invention provides contact electrodes suitable for external application to the skin of the head and being held in place by a compliant band, or by suction or by adhesion.

In a related aspect the invention provides contact electrodes either buried within the contact surfaces of a surgical retractor or applied as a flexible membrane directly beneath the retractor when in use, so that the electrode surfaces make intimate contact with the tissue undergoing retraction.

Preferably a four-electrode configuration is used wherein one pair of electrodes supplies current and the other pair detects a signal. Alternatively more than four electrodes may be used and this may allow for at least partial localisation of the injured area or areas.

In yet another broad aspect the invention comprises a method for assessment of the outcome of injury resulting in pathological processes affecting cells within a portion of an animal, including a human, comprising the steps of (a) applying a first pair of electrodes about the periphery of the portion, (b) applying a second pair of electrodes also about the periphery of the portion, (c) generating an alternating current at a known current level, (d) applying the alternating current between the second pair of electrodes, (e) detecting and measuring the alternating voltage developed between the first pair of electrodes, (f) repeatedly calculating the impedance of the portion, and (g) noting the time course of any changes in the impedance.

In a related aspect the invention comprises a method for assessment of the outcome of neural injury resulting in pathological processes affecting cells of the central nervous system of an animal, including a human, further comprising the steps of (a) applying the electrodes to the cranium, (b) repeatedly calculating the impedance of the cranium, and (c) including the time course of any changes in the impedance in evaluation of the effects of the injury, wherein a substantially elevated and maintained impedance tends to support a poor prognosis.

In a further related aspect the invention comprises a method wherein the electrodes are applied directly to the central nervous system.

In a subsidiary aspect the invention uses an alternating current at a frequency of between three Hertz and three thousand Hertz.

Preferably the frequency of the alternating current is between thirty and three hundred Hertz.

Preferably the waveform of the alternating current is substantially a square wave.

Preferably the amplitude of the alternating current is substantially hold at a value selected from the range of between 0.1 microamperes and 10 microamperes, In a further broad aspect the invention comprises a method of measuring the impedance of an object (comprising living tissue) in which the duration of substantially continuous measurement exceeds one hour.

In yet another broad aspect the invention comprises apparatus capable of determining the electrical impedance and monitoring changes of the electrical impedance of an object having intrinsic electrical activity, comprising means capable of generation of an alternating current at a known current level, means capable of measuring the voltage drop produced across a first pair of electrode means as a consequence of the passage of the alternating current between a second pair of electrode means and through the object, characterised in that the measurement means is capable of coherent detection or demodulation of the voltage developed between the first pair of electrodes.

Preferably the means capable of generation of the alternating current is capable of providing a synchronisation signal to the means capable of coherent detection, In still another broad aspect the invention provides a method for evaluation of the oedema within nervous tissue by means of the measurement of impedance.

More particularly the invention provides a method of monitoring the cerebrum in order to detect adverse cerebral events characterised in that it is a method of monitoring non-pulsatile cerebral tissue impedance.

Under this aspect the invention relates to methods wherein a patient is undergoing intensive care.

Under this aspect the invention also relates to methods wherein a patient is undergoing cardiac surgery.

Under this aspect the invention further relates to methods wherein a patient is undergoing neurosurgical retraction of the brain.

DRAWINGS

The following is a description of a preferred form of the invention, given by way of example only, with reference to the accompanying diagrams.

FIG. 1: is a block diagram of a preferred device for measuring the impedance between electrodes, showing a preferred method of connection.

Figure 2:
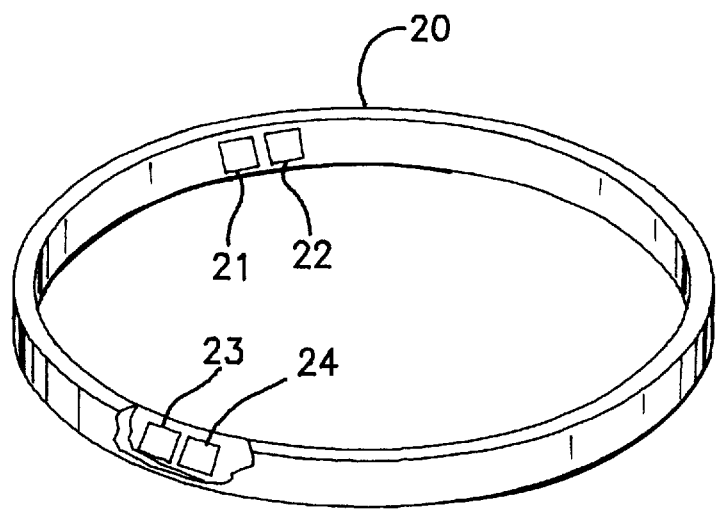

FIG. 2: is an illustration of a headband bearing an array of contact electrodes.

Figure 3:
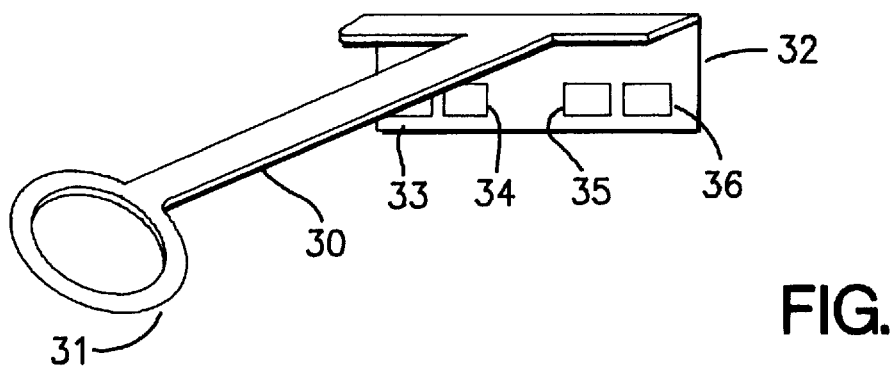

FIG. 3: is an illustration of the contact surface of a surgical retractor bearing a built-in electrode array.

Figure 4:
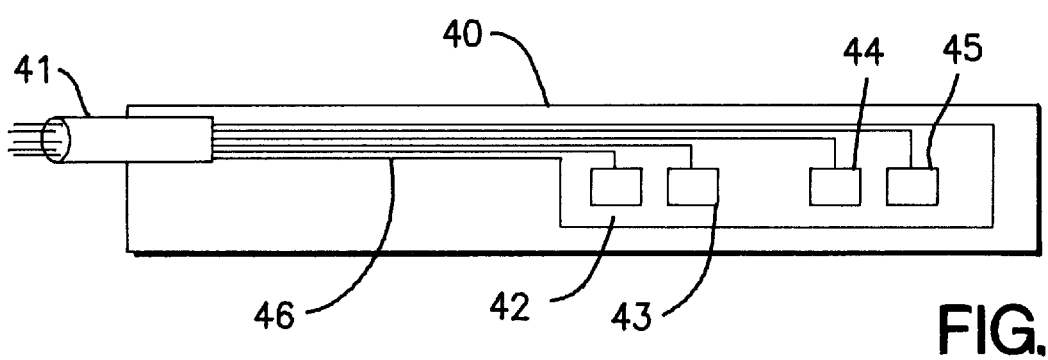
Figure 5A:
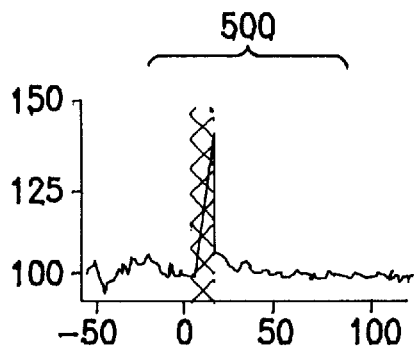
Figure 5B:
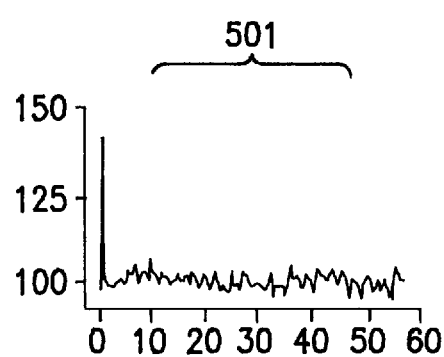
Figure 5C:
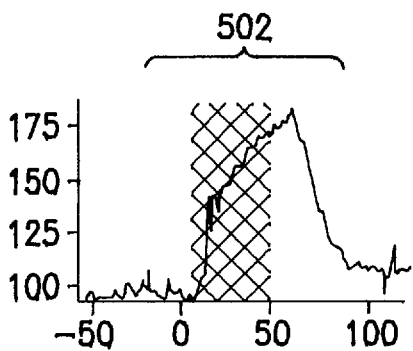
Figure 5D:
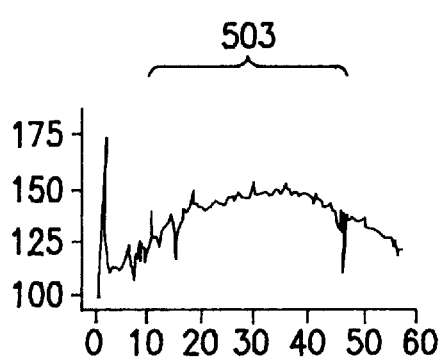

FIG. 4: is an illustration of a disposable contact electrode; a flexible membrane bearing a surface "printed" or metallised electrode array.

FIG. 5: is an illustration derived from an experimental trial, in which the duration of ischaemia is compared with the extent of impedance change over a short and a longer period.

Figure 6A:
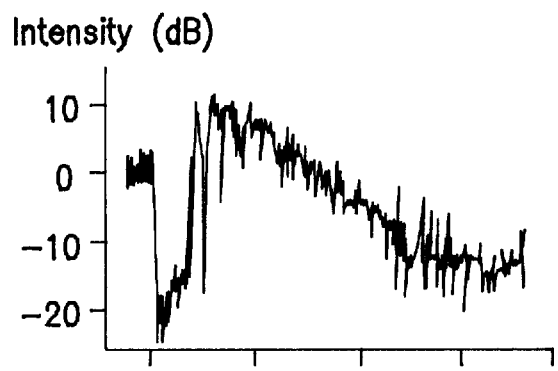
Figure 6B:
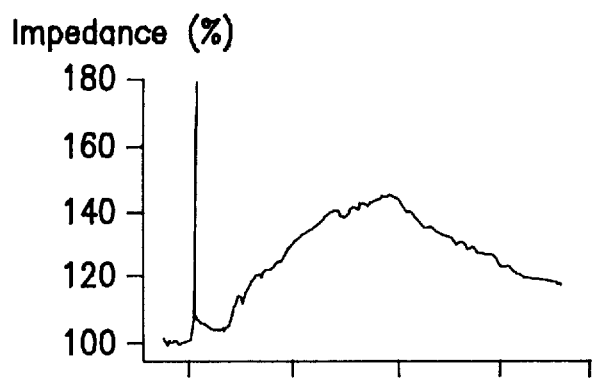
Figure 6C:
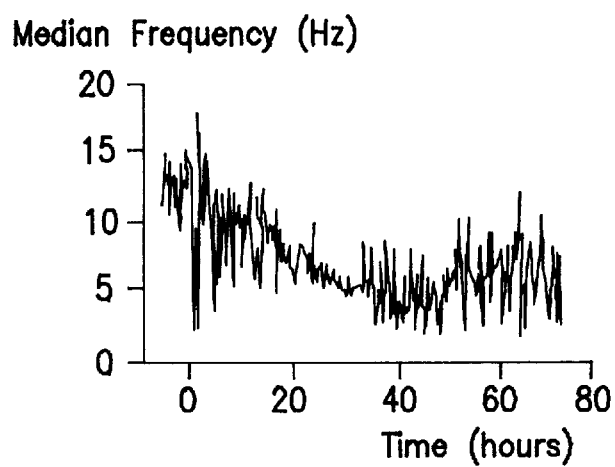

FIG. 6: is an illustration comparing EEG measurements and cortical impedance (foetal sheep).

Figure 7:
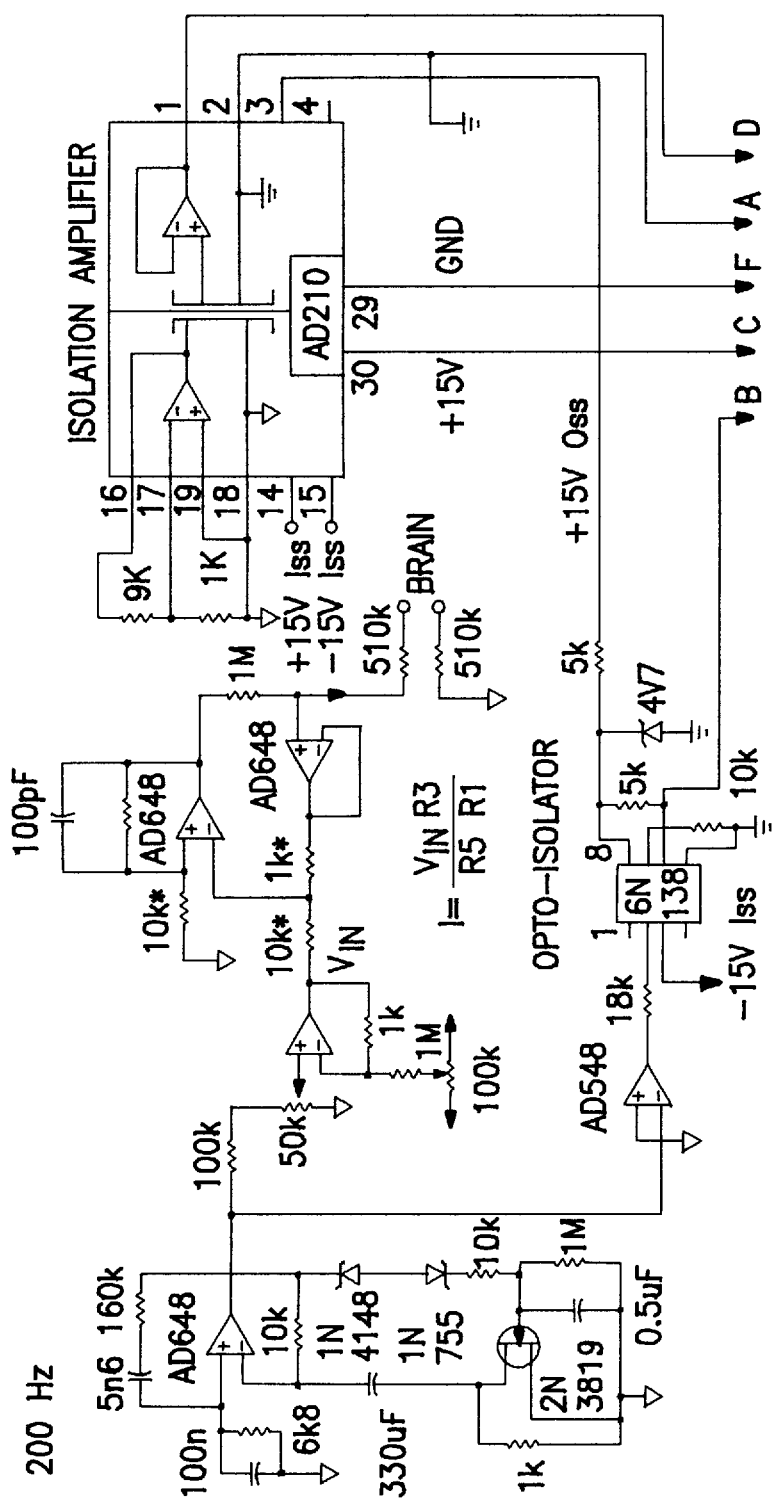

FIG. 7: is a circuit diagram of the AC current source portion of an impedance measuring device.

Figure 8:
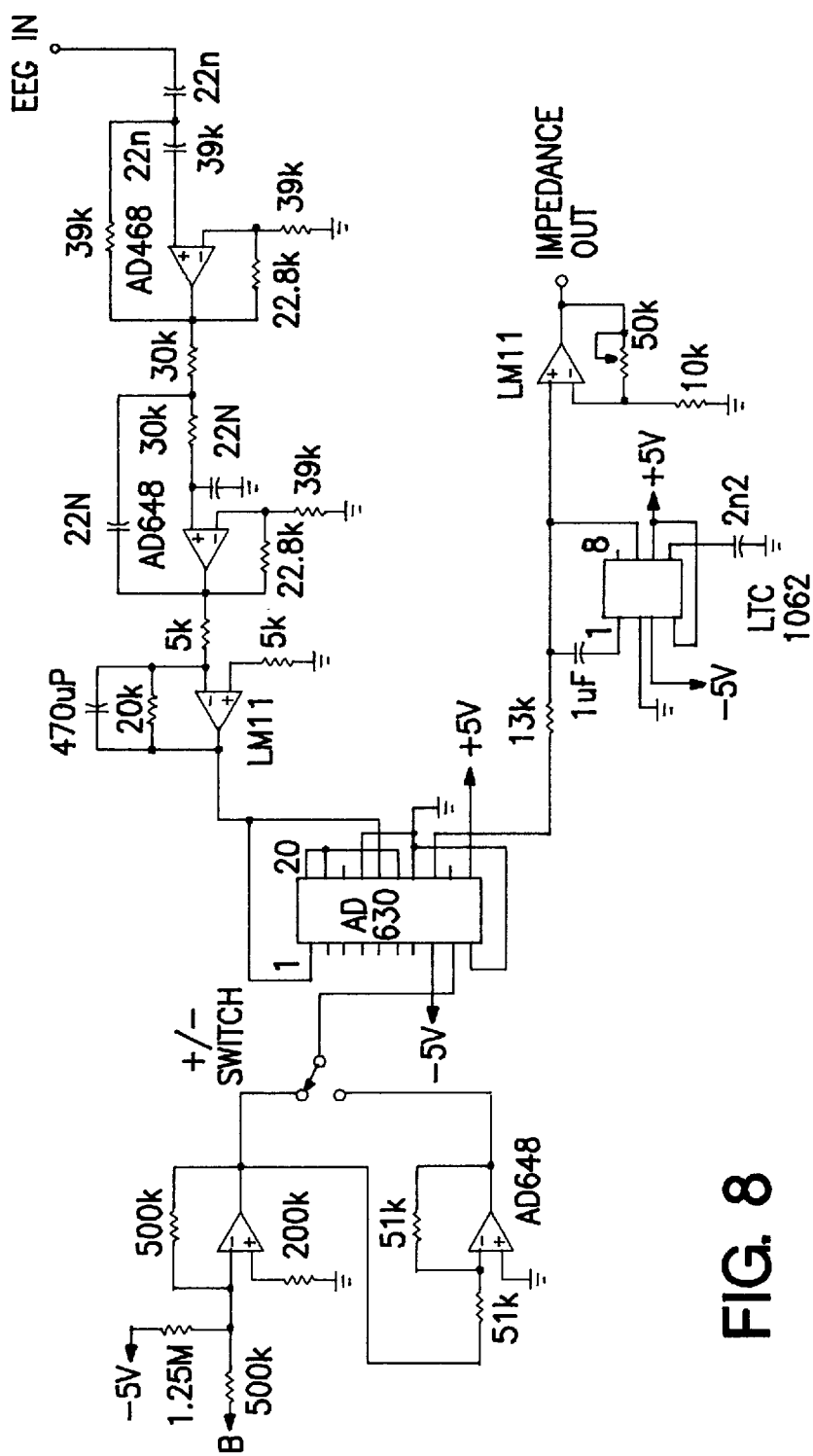
Figure 11A:
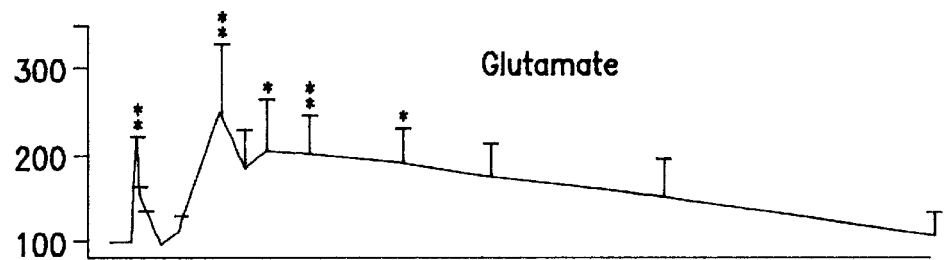
Figure 11B:
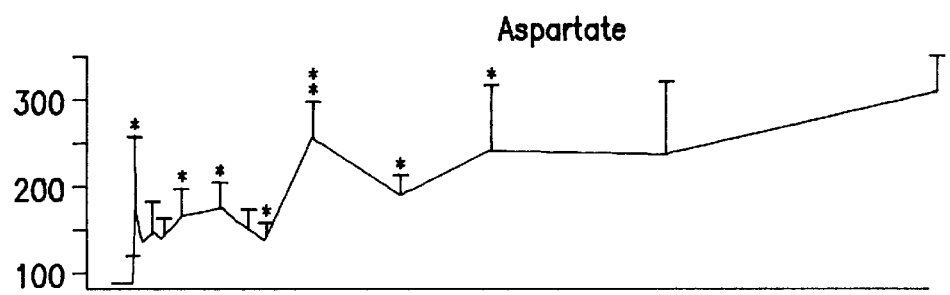
Figure 11C:
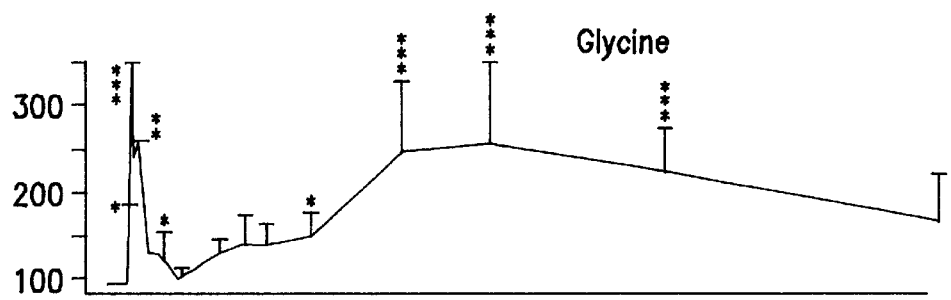
Figure 11D:
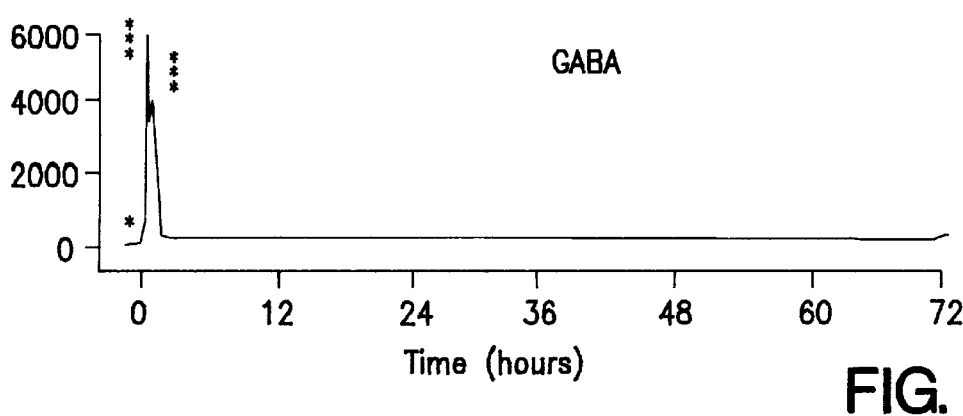

FIG. 8: is a circuit diagram of the balanced detector portion of an impedance measuring device.

Figure 9:
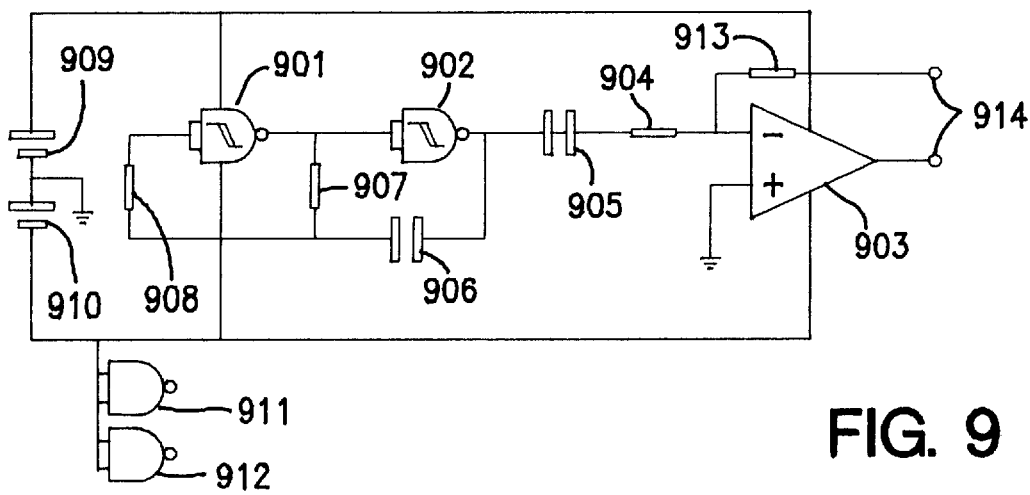

FIG. 9: is an illustration of a battery-powered stimulator for use in a telemetered impedance monitoring arrangement.

FIG. 10: is a graph comparing cortical impedance and certain amino acids as extracted from dialysate (foetal sheep).

Figure 12A:
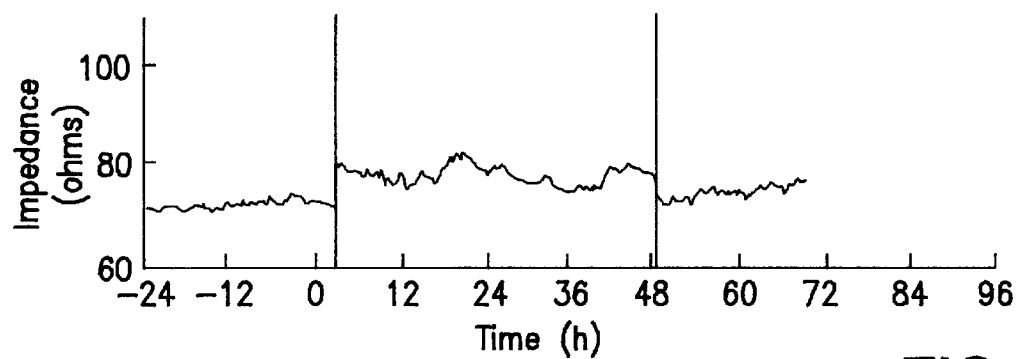
Figure 12B:
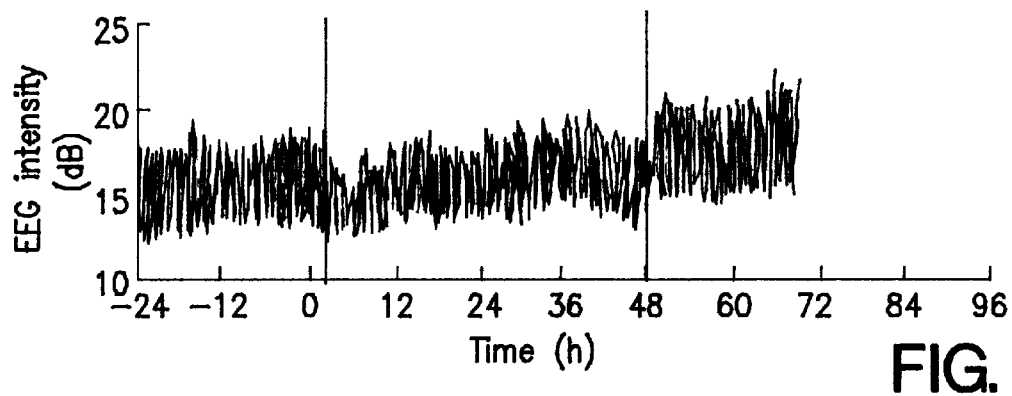
Figure 12C:
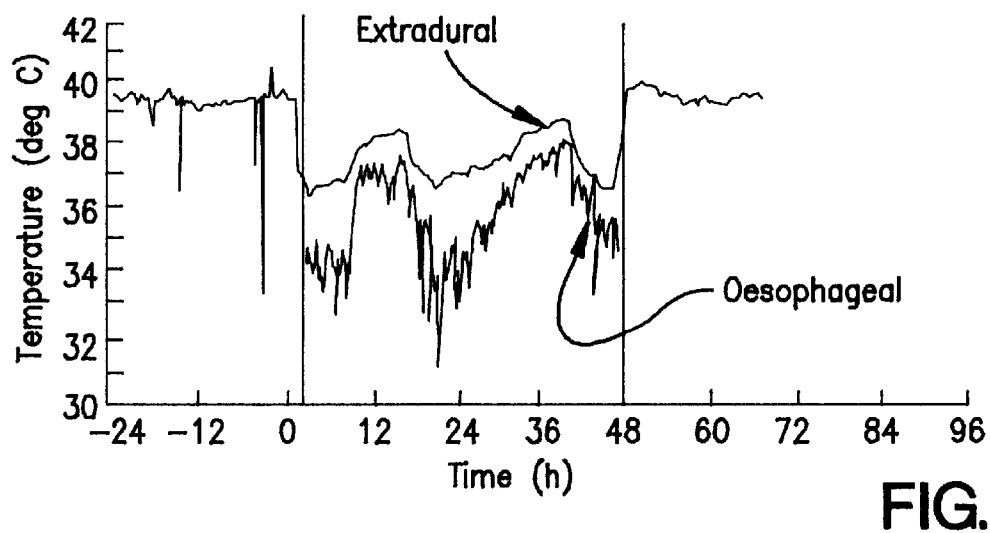

FIG. 11: is a further graph from the experiment shown in FIG. 12 (foetal sheep).

FIG. 12: is a graph of temperature, impedance, and EEG intensity (foetal sheep).

FIG. 13: is a graph of cortical impedance, EEG spectral edge frequency, and EEG intensity, of a neonatal grade III encephalopathy, with an unfavourable outcome.

FIG. 14: is a graph of cortical impedance, EEG spectral edge frequency, and EEG intensity, of a neonatal grade I encephalopathy, having a favourable outcome.

PREFERRED EMBODIMENT

Although this invention may be applied to any part of the body in which oedema of a substantial fraction of the internal tissues are liable to develop oedema, such as the thorax, most of our experiences are in relation to cerebral oedema and its measurement.

The underlying principle is believed to be that when extracellular fluid (i.e. oedema) builds up in a tissue—and in particular within nervous tissue wherein the presence of structures (such as myelinated tracts) giving a relatively low conductivity is well-described, the conductivity of the tissue rises as the ion-containing, extracellular fluid provides more conduction paths. Typical values for white matter are 700 ohm-cm and for grey matter, 300 ohm-cm. The skull is typically 5000 ohm-cm On the other hand, cytotoxic agents causing cell swelling will tend to reduce the extracellular space and hence the cross-section of relatively conductive material, and thereby cause the tissue impedance to rise. Here, the cells of particular interest are the neurones themselves, but glial cells are also likely to be important Should a given pathological process instead cause intracellular water accumulation, the tissue conductivity may actually fall and therefore the impedance will rise. For example certain cytotoxic substances may cause neuronal or glial swelling, and the extracellular space is consequently reduced. Therefore unthinking acceptance of the validity of impedance measurements as an indication of cortical normality may not be wise. On the other hand, cortical impedance measurements, in combination with other forms of assessment may assist in the differential diagnosis of a problem case.

In various experimental trials it has been shown that the extent of the rise of oedema, as monitored by impedance measurements, has been a reliable indication of the outcome of recovery. FIG. 5 illustrated this. In this Fig. the vertical axes all represent activity as a percentage of that preceding the ischaemic period. The two left-hand graphs (500, 502) show cranial impedance over a 120-minute period; the right-hand two (501, 503) show the same data (impedance) but over 60 hours. The top two graphs (500, 501) relate to a brief ischaemia (shown hatched) which did not result in long-term damage; the bottom two graphs (502, 503) relate to a longer period (40 minutes—also shown hatched) which did cause long-term damage. Presumably the clinical recording shown in FIGS. 13 and 14 similarly reflect different severity of damage.

A comparison of EEG top (intensity) and bottom (median frequency) graphs against impedance (central graph) in the same foetal brain experiment is shown in FIG. 6; it appears from this comparison that the impedance measurement is a clearer signal.

The principles of the equipment used in our preferred embodiment are that it is adapted to carry out long-term measurement of the impedance of cortical tissue using the equipment shown in the summary drawing, FIG. 1. FIG. 1 shows a cranium 101 in section, with a brain 102 within. This example has an electrically isolated current source (103) used to apply a one microampere AC square waveform, at preferably 200 Hz across a pair of electrodes (104, 105). Sensing electrodes (107, 108) are taken optionally through the amplifying section of an EEG machine if one is present, and after amplification are connected to a coherent detector (106).

A coherent detector is one that accepts an input carrying information providing the phase of the AC signal to be detected, as well as accepting an input carrying the signal itself; perhaps embedded in other, undesired signals. The detector can be created using a balanced modulator/demodulator integrated circuit. In this instance, its operation can be understood by considering the detector to comprise means to sum both positive-going and negative-going portions (converted to positive-going portions) of the received test signal, while any signals not coherent with the test signal as presented to the detector's phase input tend to cancel out and be summed to zero.

The direct (albeit isolated) connection from the source to the coherent detector carries the phase information. Impedance output changes (at 109) are usually filtered from high-frequency components, and may be displayed graphically.

This four-terminal approach has the advantage that the frequent and usual effects of resistance in the interface between the any electrode and the underlying tissues is minimised. Use of a current source provides for a known current traversing the tissue under test, and as the detected variable is an AC voltage, connection defects such as electrode potentials are rejected. The array of four electrodes may be placed either in direct contact with the tissue to be monitored as in the case of a neurosurgery—in which case a retractor of the type shown diagrammatically in FIG. 3 (incorporating electrodes which will be in contact with brain tissue which is being retracted or otherwise handled and which will deteriorate with time) may be used, or (more usually) indirect measurement through the skin and skull of an intact head may be used, with electrode within a compliant headband as shown in FIG. 2. Preferably the electrodes are of chlorided silver, or carbon, or any other suitable material used in bio-electrical electrodes. The electrodes 21,23, and 22,24 are connected via wires (not shown) to the measuring instrument. Use of a four-electrode technique renders the measurement procedure substantially independent of electrode contact resistance effects.

Alternatively more than four electrodes may be placed on a cranium (though usually only four will participate in any one measurement) and this greater number may allow for at least partial localisation of the injured area or areas. The electrode array of an EEG instrument may suffice—with some electrode pairs being "borrowed" for use in supplying the AC test current.

Preferably an alternating current is generated and monitored both for reasons of polarisation problems with DC-carrying electrodes and within tissues, and also for reasons of case of detection. Preferably the upper frequency limit of this current is somewhere between 140 and perhaps up to 3 KHz where capacitative effects become significant; 150 HZ has been found a reasonable value although preferably multiples of the power mains frequency used in the locality should be avoided, Also, dominant frequencies in an EEG are preferably avoided. Examples of these are those associated with epileptiform seizures. A (substantially) square wave AC current may be current-regulated for the majority of each cycle by active circuitry, or a sinewave current may be "regulated" or at least made into an approximation of a current source by the use of a high-voltage source with a high-value series resistance.

As capacitative loading of the electrodes is preferably avoided, higher frequencies are less suitable. A 150 Hz signal is high enough in frequency to not interfere with concurrent EEG recordings. At the low limit, frequencies of as little an 3 Hz are effective although 30 Hz upwards are preferred. Our example circuit (FIGS. 7 and 8) generates a 200 Hz signal and filters the impedance output signal with a 20 Hz low-pass filter.

In order to minimise sensing electrode polarisation, the electrodes are coupled to very high impedance preamplifiers, preferably with driven guards or shielding about the sense wires, to minimise capacitative loading.

Preferably the alternating test current is small enough to cause no physiological effects, and preferably it is further reduced by an ample safety margin, in case of delayed effects. (Some clinical cases are on the threshold of an epileptiform seizure). A current of 0.2 microamperes has been used successfully. An approximately 10–100 microvolt signal may be detected from this current level, and extracted from noise and unwanted electrical signals by techniques such as coherent detection, Previous attempts to measure cerebral impedance generally used signals developed by currents of over 100 times the above amplitude—that is, about 100 microamperes—with suitable direct AC voltmeter recordings and it is possible that such currents could trigger or exacerbate neural activity, particularly over long periods, or could cause electrode drifts.

Preferably the alternating current is developed from within an isolated, or electrically floating current generator. The two outputs from this generator are (a) an attenuated substantially square waveform applied to one of each pair of electrodes as shown in FIGS. 1 to 4, (104 and 105, 21 and 23, 33 and 36, and 42 and 44) and (b) an optically isolated, synchronising square wave for internal use in coherent signal detection.

Preferably the sensed current, picked up from a sense pair of electrodes (107 and 108, 22 and 24, 34 and 37, or 43 and 45) is amplified within a high-impedance difference amplifier capable of rejecting signals common to both inputs. It is advantageous to use the technique of coherent detection, in order to reject artefacts due to intrinsic electrical activity (EEG or ECG, for example) or external interference during the process of rectification into direct current. Preferably the common-mode rejection performance is enhanced with an isolated amplifier—though this may be most useful in monitoring acute cases in uncontrolled environments.

Because blood flow pulsations and the like influence the impedance values in measurements that resolve to within one second periods, we prefer to use a low-pass filter so that events of durations less than typically 10 or even 60 seconds are discarded.

The direct current from the low-pass filter is further amplified according to the requirements of the display medium, and is indicated to the user by a preferred means. Preferred display means include graphical displays, most preferably involving a paper record from a pen chart recorder or a simulation of one with a computer and an optional printer. Such displays allow one to interpret a reading at any particular time in the light of past trends. Alternatively, the instrument could be manufactured so as to simply show a present reading in analogue or numeric terms, or even more simply, to show by means of a visible or audible (alarm) signal when a preset threshold has been exceeded. Results have been expressed simply in terms of percentage change as referred to the normal or initial value—although quantitation is preferred Optionally a microprocessor or other numerical evaluation means may be incorporated so that the instrument can take account of such factors as the initial impedance value and/or the rate of change of impedance before presenting a measurement or an alarm signal.

The retractor shown diagrammatically as 30 in FIG. 3 may be used during neurosurgery as a retractor to apply traction to a part of the brain, while the non-toxic embedded electrodes shown as 33 . . . 36 may be connected to impedance measuring equipment of the type described above for concurrent monitoring of oedema. (Connecting wires are not shown). In use a tension applied from the left to the handle 31 causes brain tissue adjacent to the tongue 32 and its embedded electrodes 33 . . . 36 to be compressed, thereby exposing other areas. Preferably the retractor is a disposable item made of a tough, non-conducting plastic material so that electric currents are not shunted through its tongue 32. This is an idealised diagram. Other types of neurosurgical retractor may also be manufactured with similar embedded sets of electrodes. Alternatively a flexible membrane as shown in FIG. 4 might be manufactured upon a non-conducting film 40, carrying a set of surface electrodes 42, 43, 44, and 45, surrounding guard conductor 46 and connecting wires (all of which may be a pattern of deposited metal films laid down as if on a printed circuit) on one side and connected to a multiconductor wire 41; this may be placed beneath any conventional retractor with the electrodes in contact with the tissue to be monitored The assembly of FIG. 4 is preferably sterile, and disposable.

This flexible planar type of sensor array may also be useful for impedance measurements during (for example) heart surgery when the extent and effects of cardioplegia on the heart require to be monitored.

More details of the actual impedance monitor are given in FIGS. 7 and 8. FIG. 7 is the current source and comprises an isolated power supply, a low-frequency oscillator, a current source to supply a test current, and a buffer to provide a synchronising signal to the detector of FIG. 8. It corresponds to block 103 of FIG. 1. The isolated power supply is an AD210 module located at top right of the drawing, This is capable of generating an acceptable (for medical applications) dual-voltage power supply at +15V and –15V to the remainder of the circuit. (Its unused isolated analogue channels are reserved for future fault-detection purposes). Hollow triangular earth symbols are the isolated earths: parallel-line earth symbols are the non-isolated chassis earth point. Thus connectors C and E supply power to the isolation amplifier, and A and D are unused. A low-frequency oscillator operating at about 200 Hz is made from a 2N3819 unijunction transistor capacitatively coupled to an AD648 buffer and filtering amplifier. One branch of the output is fed to an AD548 used as an inverting high-gain buffer and then through a 6N138 optical isolator shown at bottom center of FIG. 7 to provide a synchronising signal (at connector b) to the detector of FIG. 8 The other branch of the output is passed through gain and offset controls to a current source comprising a pair of AD648 operational amplifiers; the upper one being a power and feedback regulating stage; sensing a buffered voltage from across the 1M ohm current-to-voltage converter and returning a signal to the input of the upper amplifier. 510K resistors limit worst-case failure currents to the brain to a maximum of about 15 $\mu$A.

FIG. 8 shows the synchronous demodulator and filtering stage used to extract a voltage (placed at "IMPEDANCE OUT") proportional to the measured impedance which is substantially free of artefactual signals from electrical interference, the electroencephalogram, muscle and heart activity, and movement artefacts. It corresponds to blocks 106 and 109 of FIG. 1.

A conventional electroencephalogram (EEG) amplifier actually detects the signals resulting from the stimulus signal. Advantages of using a conventional amplifier include that there is usually a requirement to monitor the EEG as well in clinical applications, and the same electrodes can perform both tasks. Alternatively one of the well-known differential preamplifier circuits can be used, with a frequency response limited to below about 300 Hz. The signal from this amplifier, including impedance-related component, arrives at the top right of this circuit and is fed through AC-coupled active filters and an X4 gain/buffer stage to an AD630 balanced modulator/demodulator integrated circuit (Analog Devices, USA) controlled by square-wave signals of selectable polarity coming into this circuit at input B at top left. A coherent detector such au this device in this circuit operates by repeatedly either adding or subtracting the incoming signal according to the phase of its control signal, thereby reinforcing the impedance signal developed from either polarity of test current, while averaging out any other signals. (In order to minimise interference we prefer to operate the oscillator of FIG. 7 away from dominant frequencies of either the EEG or of likely mains interference. A future device may use a variety of frequencies in order to minimise measurement artifacts An active filter (device: LTC1062) acts as a 5th order low-pass filter with a 3 dB point at 20 Hz. The impedance output at lower right is provided with a gain-settable buffer so that the output can be trimmed to match the input requirements of a chart recorder, analogue-to-digital converter, or the like.

Impedance variations typically occur at a slow rate of at most about 10% of full range per minute and the impedance signal can successfully be separated out from other signals and presented as a substantially reliable output.

FIG. 9 shows an alternative current source adapted for long-term application with a +,– 1.5V battery-driven supply (909,910). C-MOS Schmitt trigger gates 901, 902 (both ¼ CD4093) form a relaxation oscillator generating a slow AC square wave coupled through a 1 $\mu$F capacitor 905 to an output buffer amplifier. Frequency-setting parts include 907 and 908, 1 M ohms. and capacitor 906, 14.7 $\pi$F. The 150K output resistor 913 provides (with resistor 904 at 300K, 5 $\mu$A at the output 914, or with 904 at 3M, 0.5 $\mu$A). The operational amplifier is an ICL 7611. No provision is shown for a synchronising output for a synchronous detector. Unused Schmitt NAND gates 911, 912 are tied low so that their current consumption remains low. The circuit current drain is 12.5 $\mu$A giving a life of about 4 months with type 392 38 $\mu$mA/H batteries. This stimulator or current source can be used with a telemetry system.

LABORATORY ANALYSIS SOFTWARE.

A package of software has been written for use with an IBM-PC or compatible computer using "LABVIEW" (National Instruments, USA) to control real-time data acquisition, perform calibration/recalibration, carry out real-time analysis such as power spectral analysis, store results, and display information graphically—even historical information—during collection.

Modalities that may be collected over a long period, optionally displayed, and recorded in files on a hard disk after collection by the appropriate transducer or electrode array, then after amplification and signal processing include: EEG spectra, blood pressure, EKG (heartbeat) rate, body temperature, nuchal electromyogram (EMG), and impedance, For example the last hour of data may be shown during an experiment for supervisory purposes, and data may be recalled and examined in greater detail such as over a short time period, in a clinical application, a versatile status monitoring device such as this may be called on to review past data without interrupting the continuing collection of a stream of data. The recorded data is inherently compatible with transmission to a remote site for evaluation.

CLINICAL TRIALS

In order to demonstrate and clarify the meaning of impedance measurements we have carried out a number of trials using animal models, and a limited number of observations in human infants affected by perinatal asphyxia. The underlying assumption or model is that the impedance of central nervous tissue represents the volume of extracellular current-carrying paths predominantly comprising ionised fluids and if neurones are caused to swell by some abnormal process, this volume is reduced and the impedance rises, as per FIG. 5.

In relation to the "abnormal process" above, FIGS. 10 and 11 together show concurrent records from a foetal sheep experiment in which a hypoxic/ischemic insult was applied at 0 hours. This data shows impedance changes as in other experiments which are here correlated to chemical indicators of toxicity to cells within the central nervous system. Concentrations of chemicals were measured with a microdialysis/HPLC setup which sampled the extracellular fluid within the affected part of the brain. Citrulline is a by-product of nitric oxide (NO) synthesis, thus the citrulline curve is believed to be correlated with nitric oxide synthesis. The "excitotoxic index" is the product of (glutamate * glycine)/GABA and was calculated to derive a quantitative descriptor reflecting the composite magnitude of the excitatory, compared with the inhibitory neurotransmitters present generally through the CNS tissue in the region under test. This excitotoxic index is believed to be related to neuronal swelling or intracellular oedema, and pathological processes within the neurones. The similarity in trends between the excitotoxic index and the impedance suggests that the continuous measurement of impedance offers an accessible and simple method by means of which changes in the excitotoxic index can be inferred.

This experiment, like many others in our series, exhibits what appears to be a secondary phase of neuronal damage some hours after the initial insult. Note that the cortical EEG and spectral edge records show epileptiform seizure activity, (shown also by spike activity on the raw EEG) and note that the impedance rises to a peak at around 32 hours after occlusion.

FIG. 12 shows, for a sheep experiment, records of the effect of temperature on impedance. It is useful to quantify the effects of temperature particularly if mild hypothermia is likely to be used as a type of treatment. A period of reduced temperature was induced for about 44 hours. During that time the impedance shows a mall step rise which tends to mirror the extradural temperature and which substantially returns to the original value on restoration of the former temperature.

FIG. 13 shows records from a case of human neonatal asphyxia; with the horizontal axis showing time; this recording started at 2.5 hours of age. The top graph indicates the biparietal EEG intensity and a number of seizures are evident. The drug paraldehyde was administered as a high dose at the three sites marked by arrows, and the seizures were eventually quelled The EEG spectral edge (that frequency below which 95% of the EEG power exists at a given moment) also shows the presence of seizures snd after about 60 hours (3600 minutes) a trend to lower frequencies. Meanwhile the cerebral impedance graph shows a rising trend from about the time that the seizures commenced. Impedance remained at an abnormally high level from about 45 hours. This case bad an unfavourable outcome and was graded as a Grade III encephalopathy FIG. 14 (with a shorter time scale) shows records from a second case of human neonatal asphyxia; with the horizontal axis showing time. The top graph indicates the biparietal EEG intensity and no seizures are evident. The EEG spectral edge (that frequency below which 95% of the EEG power exists at a given moment) shows no seizures and the cerebral impedance graph shows a substantially constant line. This case had a favourable outcome, and was rated as a grade I encephalopathy.

Presumably a clinician would use a continuous EEG recording as a determinant of the need for medication to prevent seizures, while the impedance measurement appears to indicate damage so far; which may at least qualitatively if not quantitatively indicate the need for certain further treatments, and appears to be particularly useful in indicating the final outcome of the case, It is tempting to surmise that events occurring at the time of the seizures at about 20 hours caused neural insults resulting in intracellular oedema and possibly the seizures themselves release toxic materials; leading to the possibility that treatments having the effect of modulating neuronal activity and in particular seizures (which are often not clinically apparent as movement disorders) may be quite beneficial in management of these cases. We can say that the impedance rises when a number of seizures are occurring, and that without an EEG a clinical would probably not be aware that a seizure was occurring a all. Instrumentation is clearly useful. Further studies using cerebral impedance as a measure of "neuronal health" are continuing.

Finally, it will be appreciated that various alterations and modifications may be made to the foregoing without departing from the scope of this invention as described in this specification.

I claim:

1. A method for assessment of the outcome of brain injury resulting in pathological processes affecting cells within a portion of in animal, including a human, comprising the steps of
    (a) applying a first pair of electrodes about the periphery of the portion,
    (b) applying a second pair of electrodes also about the periphery of the portion,
    (c) generating an alternating current at a known current level, (d) applying the alternating current between the second pair of electrodes, (e) detecting and measuring the alternating voltage developed between the first pair of electrodes, (f) repeatedly calculating the impedance of the portion, and (g) noting the time course of any changes in the impedance.

2. A method as claimed in claim 1 for assessment of the outcome of neural injury resulting in pathological processes affecting cells of the central nervous system of an animal, including a human, further composing the steps of (a) applying the electrodes to the cranium, (b) repeatedly calculating the impedance of the cranium, and (c) including the time course of any changes in the impedance in evaluation of the effects of the injury, wherein a substantially elevated and maintained impedance tends to support a poor prognosis.

3. A method as claimed in claim 2 wherein the electrodes are applied directly to the central nervous system.

4. A method as claimed in claim 3 wherein the current is an alternating current at a frequency of between three Hertz and three thousand Hertz.

5. A method as claimed in claim 4 wherein the frequency of the alternating current is between thirty and three hundred Hertz.

6. A method as claimed in claim 5 in which the waveform of the alternating current is substantially a square wave.

7. A method as claimed in claim 6 wherein the amplitude of the alternating current is held substantially at a value selected from the range of between 0.1 microamperes and 10 microamperes.

8. A method as claimed in claim 7 in which the duration of substantially continuous measurement exceeds one hour.

9. Apparatus capable of determining the electrical impedance and monitoring changes of the electrical impedance of a damaged brain, comprising means capable of generation of an alternating current at a known current level, means capable of measuring the voltage drop produced across a first pair of electrode means as a consequence of the passage of the alternating current between a second pair of electrode means and through the brain, characterised in that the measurement moans is capable of coherent detection or demodulation of the voltage developed between the first pair of electrodes.

10. Apparatus as claimed in claim 9, wherein the means capable of generation of the alternating current is capable of providing a synchronisation signal to the means capable of coherent detection.

* * * * *